(12) United States Patent
Hercouet et al.

(10) Patent No.: US 7,914,591 B2
(45) Date of Patent: Mar. 29, 2011

(54) PROCESS FOR THE LIGHTENING DYEING OF KERATIN MATERIALS USING AT LEAST ONE ANHYDROUS DYEING COMPOSITION COMPRISING AT LEAST ONE ALKALINE AGENT AND AT LEAST ONE OXIDIZING COMPOSITION

(75) Inventors: Leïla Hercouet, Neuilly Plaisance (FR); Frédéric Simonet, Clichy (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/642,599

(22) Filed: Dec. 18, 2009

(65) Prior Publication Data

US 2010/0186177 A1  Jul. 29, 2010

Related U.S. Application Data

(60) Provisional application No. 61/149,104, filed on Feb. 2, 2009.

(30) Foreign Application Priority Data

Dec. 19, 2008  (FR) ...................................... 08 07298

(51) Int. Cl.
*A61Q 5/10* (2006.01)
(52) U.S. Cl. ............. 8/405; 8/406; 8/435; 8/455; 8/463; 8/111; 132/202; 132/208
(58) Field of Classification Search ............... 8/405, 406, 8/435, 455, 463, 111; 132/202, 208
See application file for complete search history.

(56) References Cited

U.S. PATENT DOCUMENTS

| | | |
|---|---|---|
| 3,100,739 A | 8/1963 | Kaiser et al. |
| 3,369,970 A | 2/1968 | McLaughlin et al. |
| 3,629,330 A | 12/1971 | Brody et al. |
| 3,861,868 A | 1/1975 | Milbrada |
| 4,138,478 A | 2/1979 | Reese et al. |
| 4,170,637 A | 10/1979 | Pum |
| 4,226,851 A | 10/1980 | Sompayrac |
| 4,357,141 A | 11/1982 | Grollier et al. |
| 4,366,099 A | 12/1982 | Gaetani et al. |
| 4,488,564 A | 12/1984 | Grollier et al. |
| 4,725,282 A | 2/1988 | Hoch et al. |
| 4,845,293 A | 7/1989 | Junino et al. |
| 5,021,066 A | 6/1991 | Aeby et al. |
| 5,259,849 A | 11/1993 | Grollier et al. |
| 5,364,414 A | 11/1994 | Lang et al. |
| 5,817,155 A | 10/1998 | Yasuda et al. |
| 6,010,541 A | 1/2000 | De La Mettrie et al. |
| 6,074,439 A | 6/2000 | De La Mettrie et al. |
| 6,129,770 A | 10/2000 | Deutz et al. |
| 6,156,713 A | 12/2000 | Chopra et al. |
| 6,165,444 A | 12/2000 | Dubief et al. |
| 6,190,421 B1 | 2/2001 | Rondeau et al. |
| 6,206,935 B1 | 3/2001 | Onitsuka et al. |
| 6,238,653 B1 | 5/2001 | Narasimhan et al. |
| 6,251,378 B1 | 6/2001 | Laurent et al. |
| 6,260,556 B1 | 7/2001 | Legrand et al. |
| 6,277,154 B1 | 8/2001 | Lorenz |
| 6,277,155 B1 | 8/2001 | De La Mettrie et al. |
| 6,365,136 B1 | 4/2002 | Lauscher et al. |
| 6,423,100 B1 | 7/2002 | Lang et al. |
| 6,447,552 B1 | 9/2002 | Golinski |
| 6,645,258 B2 | 11/2003 | Vidal et al. |
| 6,660,045 B1 | 12/2003 | Hoeffkes et al. |
| 6,695,887 B2 | 2/2004 | Cottard et al. |
| 6,800,098 B1 | 10/2004 | Allard et al. |
| 7,135,046 B2 | 11/2006 | Audousset |
| 7,153,331 B2 | 12/2006 | Desenne et al. |
| 7,217,298 B2 | 5/2007 | Legrand et al. |
| 7,285,137 B2 | 10/2007 | Vidal et al. |
| 7,442,215 B2 | 10/2008 | Audousset et al. |

(Continued)

FOREIGN PATENT DOCUMENTS

CA        1 268 421        5/1990

(Continued)

OTHER PUBLICATIONS

French Search Report for FR 0807298, dated Nov. 2, 2009. Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.

(Continued)

*Primary Examiner* — Eisa B Elhilo
(74) *Attorney, Agent, or Firm* — Finnegan, Henderson, Farabow, Garrett & Dunner

(57) ABSTRACT

Provided is a process for dyeing keratin materials, comprising applying to the keratin materials: a) at least one anhydrous composition (A) comprising at least one fatty substance, at least one surfactant, at least one alkaline agent, and at least one colored or coloring species; and b) at least one aqueous composition (B) comprising at least one oxidizing agent; wherein: the at least one fatty substance is present in the at least one anhydrous composition (A) in an amount of greater than 20% by weight, relative to the total weight of the at least one anhydrous composition (A); and the at least one colored or coloring species comprises at least one oxidation dye and/or at least one direct dye; on the condition that when the at least one anhydrous composition (A) comprises, as the at least one colored or coloring species, only at least one direct dye, the at least one fatty substance is present in an amount ranging from 40 to 80% by weight, relative to the total weight of the at least one anhydrous composition (A). Also provided is a multi-compartment device comprising: the composition (A) and the composition (B) as defined above.

25 Claims, No Drawings

U.S. PATENT DOCUMENTS

| | | |
|---|---|---|
| 7,458,993 B2 | 12/2008 | Cottard et al. |
| 7,494,513 B2 | 2/2009 | Kravtchenko et al. |
| 7,575,605 B2 | 8/2009 | Legrand |
| 7,651,533 B2 | 1/2010 | Legrand |
| 7,651,536 B2 | 1/2010 | Cottard et al. |
| 7,766,977 B2 | 8/2010 | Cottard et al. |
| 7,799,095 B2 | 9/2010 | Mario et al. |
| 2003/0190297 A1 | 10/2003 | Narasimhan et al. |
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0181883 A1 | 9/2004 | Legrand et al. |
| 2004/0226110 A1 | 11/2004 | LeGrand |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1 | 11/2006 | Legrand |
| 2007/0006397 A1 | 1/2007 | Schmenger et al. |
| 2007/0033743 A1* | 2/2007 | Kravtchenko ............ 8/405 |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 438 951 | 7/2004 |
| EP | 1 449 512 | 8/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 474 | 1/2009 |
| EP | 2 018 848 | 1/2009 |
| EP | 2 072 034 | 6/2009 |
| EP | 2 072 035 | 6/2009 |
| EP | 2 072 036 | 6/2009 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 | 8/2001 |

| | | |
|---|---|---|
| WO | WO 02/89748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2008/138844 | 11/2008 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/642,593, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 38 14 356, dated Sep. 8, 1988.
English language Abstract of DE 43 09 509, dated Sep. 19, 1994.
English language Abstract of EP 1 023 891, dated Aug. 2, 2000.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/006418, dated Jan. 18, 2007.
English language Abstract of WO 2007/096027, dated Aug. 30, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
European Search Report for EP 10 15 5935, dated Octoer 8, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.

Notice of Allowance mailed Aug. 27, 2010, in U.S. Appl. No. 12/642,513.
Notice of Allowance mailed in co-pending U.S. Appl. No. 12/339,753, dated Jul. 9, 2010.
Notice of Allowance mailed Jun. 11, 2010, in U.S. Appl. No. 12/642,489.
Notice of Allowance mailed Nov. 19, 2010, in U.S. Appl. No. 12/339,820.
Notice of Allowance mailed Nov. 26, 2010, in U.S. Appl. No. 12/642,513.
Notice of Allowance mailed Nov. 26, 2010, in U.S. Appl. No. 12/642,543.
Notice of Allowance mailed Oct. 26, 2010, in U.S. Appl. No. 12/339,753.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.

* cited by examiner

PROCESS FOR THE LIGHTENING DYEING OF KERATIN MATERIALS USING AT LEAST ONE ANHYDROUS DYEING COMPOSITION COMPRISING AT LEAST ONE ALKALINE AGENT AND AT LEAST ONE OXIDIZING COMPOSITION

This application claims benefit of U.S. Provisional Application No. 61/149,104, filed Feb. 2, 2009. This application also claims benefit of priority under 35 U.S.C. §119 to French Patent Application No. 0807298, filed Dec. 19, 2008.

Provided is a process for the lightening-dyeing of human keratin materials, such as the hair.

Processes for lightening keratin materials such as human keratin fibers often involve applying an aqueous composition comprising at least one oxidizing agent, under alkaline pH conditions. This oxidizing agent has the role of degrading the melanin of the hair, which, depending on the nature of the oxidizing agent present, may lead to a more or less pronounced lightening of the fibers. Thus, for relatively weak lightening, the oxidizing agent is often hydrogen peroxide. When greater lightening is sought, peroxygenated salts, for instance persulfates, in the presence of hydrogen peroxide may be used.

The lightening process may be performed under alkaline conditions, and an alkaline agent commonly used is aqueous ammonia. Aqueous ammonia may allow the pH of the composition to be adjusted to an alkaline pH to enable activation of the oxidizing agent. This oxidizing agent may cause swelling of the keratin fiber, with lifting of the scales, which promotes the penetration of the oxidizing agent into the fiber, and thus may increase the efficacy of the reaction.

However, aqueous ammonia is volatile, which users find disagreeable due to the characteristic strong, rather unpleasant odor of ammonia that is given off during the process.

Furthermore, the amount of ammonia given off requires the use of higher contents than necessary in order to compensate for the loss. Thus, the user may be inconvenienced by the odor and confronted with greater risks of intolerance, for instance irritation of the scalp (stinging).

Replacing all or some of the aqueous ammonia with one or more other standard alkaline agents may not lead to compositions that are as efficient as those based on aqueous ammonia, for example because standard alkaline agents may not afford sufficient lightening of pigmented fibers in the presence of the oxidizing agent.

In the context of dyeing hair, an oxidizing composition may be used to dye the hair permanently, starting from dye precursors such as oxidation bases and couplers. Within the context of direct dyeing, although an oxidizing agent may not be required to develop the coloration, one may be used to obtain, along with the coloration, a lightening effect. Such a process is then referred to as "direct dyeing" or "semipermanent dyeing under lightening conditions."

Thus, provided are dyeing processes performed in the presence of at least one oxidizing agent, which may not have the drawbacks of the existing processes, while at the same time may remain at least as efficient, as regards the dyeing power obtained, the chromaticity, and the homogeneity of the coloration along the fiber.

Provided therefore is a process for dyeing keratin materials, comprising applying to the keratin materials:
(a) at least one anhydrous composition (A) comprising at least one fatty substance, at least one surfactant, at least one alkaline agent, and at least one colored or coloring species; and
(b) at least one aqueous composition (B) comprising at least one oxidizing agent;
wherein:
the at least one fatty substance is present in the at least one anhydrous composition (A) in an amount of greater than 20% by weight, relative to the total weight of the at least one anhydrous composition (A); and
the at least one colored or coloring species comprises at least one oxidation dye and/or at least one direct dye;
provided that when the at least one anhydrous composition (A) comprises, as the at least one colored or coloring species, only at least one direct dye, the at least one fatty substance is present in an amount ranging from 40 to 80% by weight, relative to the total weight of the at least one anhydrous composition (A).

Also provided is a multi-compartment device comprising:
a first compartment comprising at least one anhydrous composition (A) comprising at least one fatty substance, at least one surfactant, at least one alkaline agent, and at least one colored or coloring species; and
a second compartment comprising at least one aqueous composition (B) comprising at least one oxidizing agent;
wherein:
the at least one fatty substance is present in the at least one anhydrous composition (A) in an amount of greater than 20% by weight, relative to the total weight of the at least one anhydrous composition (A); and
the at least one colored or coloring species comprises at least one oxidation dye and/or at least one direct dye;
provided that when the at least one anhydrous composition (A) comprises, as the at least one colored or coloring species, only at least one direct dye, the at least one fatty substance is present in an amount ranging from 40 to 80% by weight, relative to the total weight of the at least one anhydrous composition (A).

In the text herein, and unless otherwise indicated, the limits of a range of values are included in that range.

The keratin materials treated by the process described herein may, for example, be the skin and the hair. The process described herein may make it possible, for example, to obtain a good level of lightening of keratin materials such as the hair, without giving off an odor of ammonia, which may be an irritant.

As used herein, the term "anhydrous composition" means a cosmetic composition that does not contain water or that has a water content ranging from zero to less than 3% by weight, for example less than 2% by weight, such as less than 1% by weight, relative to the weight of the anhydrous composition. The water may for example be bound water, such as the water of crystallization of salts, or traces of water absorbed by the raw materials used in the production of the anhydrous compositions described herein.

The at least one anhydrous composition (A) comprises at least one fatty substance.

As used herein, the term "fatty substance" means an organic compound that is insoluble in water at ordinary temperature (25° C.) and at atmospheric pressure (760 mmHg) (solubility of less than 5%, for example 1%, such as 0.1%). In some embodiments, the at least one fatty substance may present in its structure at least one chain of at least two siloxane groups or at least one hydrocarbon-based chain having at least 6 carbon atoms. In addition, in some embodiments, the at least one fatty substance may be generally soluble in organic solvents under the same temperature and pressure conditions, for instance chloroform, ethanol, benzene, liquid petroleum jelly, or decamethylcyclo-pentasiloxane.

In some embodiments, the at least one fatty substance may for example be chosen from lower alkanes, fatty alcohols, fatty acids, fatty acid esters, fatty alcohol esters, mineral, plant, animal or synthetic oils, for example non-silicone mineral, plant, animal or synthetic oils, non-silicone waxes, and silicones.

In some embodiments, the fatty alcohols, fatty esters and fatty acids may for example contain at least one linear or branched, saturated or unsaturated hydrocarbon-based group having 6 to 30 carbon atoms, which is optionally substituted, for example with at least one hydroxyl group (such as 1 to 4). If they are unsaturated, in some embodiments, these compounds may comprise one to three conjugated or nonconjugated carbon-carbon double bonds.

As regards lower alkanes, these alkanes comprise from 6 to 16 carbon atoms and are linear or branched, optionally cyclic. By way of example, the alkanes may be chosen from hexane, undecane, dodecane, tridecane, and isoparaffins such as isohexadecane and isodecane.

As non-silicone oils that may be used in the process described herein, non-limiting examples that may be mentioned include:
  hydrocarbon-based oils of animal origin, such as perhydrosqualene;
  hydrocarbon-based oils of plant origin, such as liquid fatty acid triglycerides having from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names MIGLYOL® 810, 812 and 818 by the company Dynamit Nobel, jojoba oil, and shea butter oil;
  linear or branched hydrocarbons of more than 16 carbon atoms and of mineral or synthetic origin, such as liquid paraffins and derivatives thereof, petroleum jelly, liquid petroleum jelly, hydrogenated polyisobutenes such as PARLEAM®, for example liquid paraffins, petroleum jelly, liquid petroleum jelly, polydecenes and hydrogenated polyisobutenes such as PARLEAM;
  partially hydrocarbon-based fluoro oils; fluoro oils that may also be mentioned for example include perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

In some embodiments, the fatty alcohols which may be used in the process described herein are not be oxyalkylenated. In some embodiments, they are saturated or unsaturated, linear or branched. In some embodiments, they contain from 6 to 30 carbon atoms, for example from 8 to 30 carbon atoms. Non-limiting mention may be made of cetyl alcohol, stearyl alcohol, and the mixture thereof (cetylstearyl alcohol), octyl-dodecanol, 2-butyloctanol, 2-hexyldecanol, 2-undecylpentadecanol, oleyl alcohol, and linoleyl alcohol.

In some embodiments, the non-silicone waxes which may be used in the process described herein may be chosen for example from carnauba wax, candelilla wax, esparto grass wax, paraffin wax, ozokerites, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy starting materials that may be used are for example marine waxes such as the product sold by the company Sophim under the reference M82, and polyethylene waxes or polyolefin waxes in general.

In some embodiments, the fatty acids which may be used in the process described herein may be saturated or unsaturated. In some embodiments, the fatty acids contain from 6 to 30 carbon atoms, for example from 9 to 30 carbon atoms. They for example, in some embodiments, may be chosen from myristic acid, palmitic acid, stearic acid, behenic acid, oleic acid, linoleic acid, linolenic acid, and isostearic acid.

In some embodiments, the esters may be esters of saturated or unsaturated, linear or branched C1-C26 aliphatic mono- or polyacids and of saturated or unsaturated, linear or branched C1-C26 aliphatic mono- or polyalcohols, the total carbon number of the esters being for example greater than or equal to 10.

Among the monoesters, non-limiting mention may be made of dihydroabietyl behenate; octyldodecyl behenate; isocetyl behenate; cetyl lactate; C12-C15 alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, and 2-hexyldecyl laurate.

In some embodiments, esters of C4-C22 dicarboxylic or tricarboxylic acids and of C1-C22 alcohols and esters of mono-, di- or tricarboxylic acids and of C2-C26 di-, tri-, tetra- or pentahydroxy alcohols may also be used.

The following non-limiting examples may also be mentioned: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate and cetyl octanoate may for example be used.

The composition described herein may also comprise, as fatty ester, sugar esters and diesters of C6-C30 and for instance C12-C22 fatty acids. The term "sugar" means, as used herein, oxygen-bearing hydrocarbon-based compounds having several alcohol functions, with or without aldehyde or ketone functions, and which contain at least 4 carbon atoms. These sugars may be monosaccharides, oligosaccharides, or polysaccharides.

Non-limiting examples of sugars that may be mentioned include sucrose (or saccharose), glucose, galactose, ribose, fucose, maltose, fructose, mannose, arabinose, xylose and lactose, and the derivatives thereof, for example alkyl derivatives, such as methyl derivatives, for instance methylglucose.

In some embodiments, the sugar esters of fatty acids may be chosen for example from the group comprising the esters or mixtures of esters of sugars described herein and of linear or branched, saturated or unsaturated C6-C30 and for example C12-C22 fatty acids. If they are unsaturated, these compounds may comprise one to three conjugated or nonconjugated carbon—carbon double bonds.

In some embodiments, the esters may also be chosen from mono-, di-, tri-, tetraesters and polyesters, and mixtures thereof.

In some embodiments, the esters may be chosen, for example, from oleates, laurates, palmitates, myristates, behenates, cocoates, stearates, linoleates, linolenates, caprates and arachidonates, and mixtures thereof such as, for example, oleo-palmitate, oleo-stearate, and palmito-stearate mixed esters.

In some embodiments, monoesters and diesters and for example sucrose, glucose, or methylglucose mono- or dioleates, stearates, behenates, oleopalmitates, linoleates, linolenates, and oleostearates for example may be used.

A non-limiting example that may be mentioned is the product sold under the name GLUCATE® DO by the company Amerchol, which is a methylglucose dioleate.

Non-limiting examples of esters or mixtures of esters of sugar and of fatty acid that may also be mentioned include:
the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
the products sold under the name RYOTO SUGAR ESTERS, for example referenced 8370 and corresponding to sucrose behenate formed from 20% monoester and 80% di-triester-polyester; and
the sucrose mono-dipalmito-stearate sold by the company Goldschmidt under the name TEGOSOFT® PSE.

In some embodiments, the silicones that may be used in the process described herein may be volatile or nonvolatile, cyclic, linear or branched silicones, which are unmodified or modified with organic groups, having a viscosity from 5×10-6 to 2.5 m2/s at 25° C., such as 1×10-5 to 1 m2/s.

In some embodiments, the silicones that may be used in the process described herein may be in the form of oils, waxes, resins, or gums.

In some embodiments, the silicone may be chosen from polydialkylsiloxanes, such as polydimethylsiloxanes (PDMS), and organomodified polysiloxanes comprising at least one functional group chosen from poly(oxyalkylene) groups, amino groups, and alkoxy groups.

In some embodiments, the organopolysiloxanes are defined in greater detail in Walter Noll's "Chemistry and Technology of Silicones" (1968) Academic Press. They can be volatile or nonvolatile.

When they are volatile, in some embodiments, the silicones may for example be chosen from those having a boiling point ranging from 60° C. to 260° C., and for example from:
(i) cyclic polydialkylsiloxanes having from 3 to 7 and for example 4 to 5 silicon atoms. These are, for example, octamethylcyclotetrasiloxane sold under the name VOLATILE SILICONE® 7207 by Union Carbide or SILBIONE® 70045 V 2 by Rhodia, decamethylcyclopentasiloxane sold under the name VOLATILE SILICONE® 7158 by Union Carbide, and SILBIONE® 70045 V 5 by Rhodia, and mixtures thereof.

Non-limiting mention may also be made of cyclocopolymers of the dimethylsiloxane/methylalkylsiloxane type, such as VOLATILE SILICONE® FZ 3109 sold by the company Union Carbide, of formula:

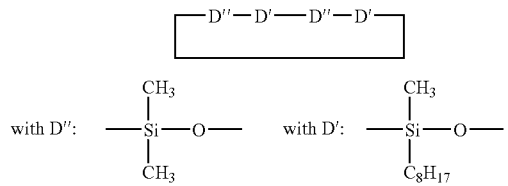

Non-limiting mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;
(ii) linear volatile polydialkylsiloxanes having 2 to 9 silicon atoms and having a viscosity of less than or equal to 5×10-6 m2/s at 25° C. An example is decamethyltetrasiloxane sold under the name SH 200 by the company Toray Silicone. Silicones belonging to this category are also described in the article published in Cosmetics and Toiletries, Vol. 91, Jan. 76, pp. 27-32, Todd & Byers "Volatile Silicone Fluids for Cosmetics."

In some embodiments, nonvolatile polydialkylsiloxanes, polydialkylsiloxane gums and resins, polyorganosiloxanes modified with organofunctional groups above, and mixtures thereof, may for example be used.

In some embodiments, these silicones may for example be chosen from polydialkylsiloxanes, among which non-limiting mention may be made of polydimethylsiloxanes having trimethylsilyl end groups. The viscosity of the silicones may be measured, for example, at 25° C. according to ASTM standard 445 Appendix C.

Among these polydialkylsiloxanes, mention may be made, in a nonlimiting manner, of the following commercial products:
the SILBIONE® oils of the 47 and 70 047 series or the MIRASIL® oils sold by Rhodia, for instance the oil 70 047 V 500 000;
the oils of the MIRASIL® series sold by the company Rhodia;
the oils of the 200 series from the company Dow Corning, such as DC200 with a viscosity of 60 000 mm2/s;
the VISCASIL® oils from General Electric and certain oils of the SF series (SF 96, SF 18) from General Electric.

Non-limiting mention may also be made of polydimethylsiloxanes having dimethylsilanol end groups known under the name Dimethiconol (CTFA), such as the oils of the 48 series from the company Rhodia.

In this category of polydialkylsiloxanes, non-limiting mention may also be made of the products sold under the names ABIL WAX® 9800 and 9801 by the company Goldschmidt, which are poly(C1-C20)dialkylsiloxanes.

In some embodiments, the silicone gums that can be used in the process described herein may be for example polydialkylsiloxanes, such as polydimethylsiloxanes with high number-average molecular masses ranging from 200,000 to 1,000,000, used alone or as a mixture in a solvent. In some embodiments, this solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, and mixtures thereof.

In some embodiments, products that can be used for example in the process described herein are mixtures such as:
  mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;
  mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;
  mixtures of two PDMSs with different viscosities, for example a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5 \times 10^{-6}$ m$^2$/s. This product may for example contain 15% SE 30 gum and 85% SF 96 oil.

In some embodiments, the organopolysiloxane resins that can be used in the process described herein may be for example crosslinked siloxane systems having the following units:

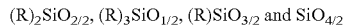

$(R)_2SiO_{2/2}, (R)_3SiO_{1/2}, (R)SiO_{3/2}$ and $SiO_{4/2}$ wherein each R independently represents a hydrocarbon-based group having 1 to 16 carbon atoms. Among these products, those in which each R independently denotes a $C_1$-$C_4$ lower alkyl radical, such as methyl, may for example be used.

In some embodiments, among these resins, non-limiting mention may be made of the product sold under the name Dow Corning 593 or those sold under the names SILICONE FLUID SS 4230 and SS 4267 by the company General Electric, which are silicones of dimethyl/trimethyl siloxane structure.

Non-limiting mention may also be made of the trimethyl siloxysilicate type resins sold for example under the names X22-4914, X21-5034 and X21-5037 by the company Shin-Etsu.

The organomodified silicones that can be used in the process described herein are for example silicones as defined above and comprising in their structure at least one organofunctional group attached via a hydrocarbon-based radical.

Besides the silicones described above, the organomodified silicones may for example be polydiarylsiloxanes, such as polydiphenylsiloxanes, and polyalkylarylsiloxanes functionalized with the organofunctional groups mentioned previously.

The polyalkylarylsiloxanes may be chosen for example from linear and/or branched polydimethyl/methylphenylsiloxanes and polydimethyl/diphenylsiloxanes with a viscosity ranging from $1 \times 10^{-5}$ to $5 \times 10^{-2}$ m$^2$/s at 25° C.

Among these polyalkylarylsiloxanes, non-limiting examples that may be mentioned include the products sold under the following names:
  the SILBIONE® oils of the 70 641 series from Rhodia;
  the oils of the RHODOURSIL® 70 633 and 763 series from Rhodia;
  the oil Dow Corning 556 Cosmetic Grade Fluid from Dow Corning;
  the silicones of the PK series from Bayer, such as the product PK20;
  the silicones of the PN and PH series from Bayer, such as the products PN1000 and PH1000;
  certain oils of the SF series from General Electric, such as SF 1023, SF 1154, SF 1250 and SF 1265.

Among the organomodified silicones, non-limiting mention may be made of polyorganosiloxanes comprising:
  polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET® L 722, L 7500, L 77 and L 711 by the company Union Carbide, and the $(C_{1-2})$alkylmethicone copolyol sold by the company Dow Corning under the name Q2 5200;
  substituted or unsubstituted amine groups, such as the products sold under the name GP 4 SILICONE FLUID and GP 7100 by the company Genesee, or the products sold under the names Q2 8220 and Dow Corning 929 or 939 by the company Dow Corning. The substituted amine groups may, for example, be $C_1$-$C_4$ aminoalkyl groups;
  alkoxylated groups such as the product sold under the name SILICONE COPOLYMER F-755 by SWS Silicones, and ABIL WAX® 2428, 2434 and 2440 by the company Goldschmidt.

In some embodiments, the at least one fatty substance may be non-oxyalkylenated or non-glycerolated.

In some embodiments, the at least one fatty substance may be chosen from compounds that are liquid or pasty at room temperature and at atmospheric pressure.

In some embodiments, the at least one fatty substance may be a compound that is liquid at a temperature of 25° C. and at atmospheric pressure.

In some embodiments, the at least one fatty substance is different from the fatty acids.

The at least one fatty substance may for example be chosen from lower alkanes, fatty alcohols, fatty acid esters, fatty alcohol esters, oils, such as mineral, plant or synthetic non-silicone oils, and silicones.

In some embodiments, the at least one fatty substance of the at least one anhydrous composition (A) may be non-siliconated.

In some embodiments, the at least one fatty substance may be chosen from liquid petroleum jelly, polydecenes, liquid esters of fatty acids or of fatty alcohols, or mixtures thereof; for example, the at least one fatty substance of the at least one anhydrous composition (A) described herein may be non-silicone.

In some embodiments, the at least one anhydrous composition (A) comprises at least 20% of fatty substance. For example, the at least one fatty substance may be present in an amount ranging from 20% to 95%, such as from 40% to 80% by weight, relative to the total weight of the at least one anhydrous composition (A).

In some embodiments, the at least one anhydrous composition (A) also comprises at least one surfactant.

In some embodiments, the at least one surfactant may be chosen from at least one nonionic surfactant and at least one anionic surfactant.

In some embodiments, the at least one anionic surfactant may for example be chosen from the salts (for example alkali metal salts, such as sodium salts, ammonium salts, amine salts, amino alcohol salts or alkaline-earth metal salts such as magnesium salts) of the following compounds:

- alkyl sulfates, alkyl ether sulfates, alkylamido ether sulfates, alkylaryl polyether sulfates, and monoglyceride sulfates;
- alkylsulfonates, alkylamidesulfonates, alkylarylsulfonates, α-olefin sulfonates, and paraffin sulfonates;
- alkyl phosphates and alkyl ether phosphates;
- alkylsulfosuccinates, alkyl ether sulfosuccinates, and alkylamidesulfosuccinates;
- alkylsulfoacetates;
- acylsarcosinates; acylisethionates, and N-acyltaurates;
- salts of fatty acids such as oleic acid, ricinoleic acid, palmitic acid or stearic acid, coconut oil acid or hydrogenated coconut oil acid;
- alkyl-D-galactoside uronic acid salts;
- acyllactylates;
- salts of polyoxyalkylenated alkyl ether carboxylic acids, of polyoxyalkylenated alkylaryl ether carboxylic acids or of polyoxyalkylenated alkylamido ether carboxylic acids, for instance those having from 2 to 50 ethylene oxide groups;
- and mixtures thereof.

It should be noted that the alkyl or acyl radical of these various compounds may for example contain from 6 to 24 carbon atoms, such as from 8 to 24 carbon atoms, and the aryl radical may for example denote a phenyl or benzyl group.

The at least one nonionic surfactant may for example be chosen from monooxyalkylenated, polyoxyalkylenated, monoglycerolated and polyglycerolated nonionic surfactants. The oxyalkylene units may for example be oxyethylene or oxypropylene units, or a combination thereof, for example oxyethylene units.

Non-limiting examples of oxyalkylenated nonionic surfactants that may be mentioned include:

- oxyalkylenated ($C_8$-$C_{24}$)alkylphenols,
- saturated or unsaturated, linear or branched, oxyalkylenated $C_8$-$C_{30}$ alcohols,
- saturated or unsaturated, linear or branched, oxyalkylenated $C_8$-$C_{30}$ amides,
- esters of saturated or unsaturated, linear or branched, $C_8$-$C_{30}$ acids and of polyethylene glycols,
- polyoxyethylenated esters of saturated or unsaturated, linear or branched, $C_8$-$C_{30}$ acids and of sorbitol,
- saturated or unsaturated, oxyethylenated plant oils,
- condensates of ethylene oxide and/or of propylene oxide, inter alia, alone or as mixtures.

In some embodiments, these surfactants may contain a number of moles of ethylene oxide and/or of propylene oxide ranging from 1 to 50 such as from 2 to 30. In some embodiments, the at least one nonionic surfactant does not comprise any oxypropylene units.

In some embodiments, the oxyalkylenated nonionic surfactants may for example be chosen from oxyethylenated C8-C30, such as C18-C30, alcohols.

Non-limiting examples of ethoxylated fatty alcohols that may be mentioned include adducts of ethylene oxide with lauryl alcohol, for example those comprising from 9 to 50 oxyethylene groups and for instance those comprising from 10 to 12 oxyethylene groups (Laureth-10 to Laureth-12 in CTFA names); adducts of ethylene oxide with behenyl alcohol, for example those comprising from 9 to 50 oxyethylene groups (Beheneth-9 to Beheneth-50 in CTFA names); adducts of ethylene oxide with cetostearyl alcohol (mixture of cetyl alcohol and stearyl alcohol), for example those comprising from 10 to 30 oxyethylene groups (Ceteareth-10 to Ceteareth-30 in CTFA names); adducts of ethylene oxide with cetyl alcohol, for example those comprising from 10 to 30 oxyethylene groups (Ceteth-10 to Ceteth-30 in CTFA names); adducts of ethylene oxide with stearyl alcohol, for example those comprising from 10 to 30 oxyethylene groups (Steareth-10 to Steareth-30 in CTFA names); adducts of ethylene oxide with isostearyl alcohol, for example those comprising from 10 to 50 oxyethylene groups (Isosteareth-10 to Isosteareth-50 in CTFA names); and mixtures thereof.

Non-limiting examples of ethoxylated fatty acids that may be mentioned include the adducts of ethylene oxide with lauric, palmitic, stearic or behenic acid, and mixtures thereof, for example those comprising from 9 to 50 oxyethylene groups, such as PEG-9 to PEG-50 laurates (CTFA names: PEG-9 laurate to PEG-50 laurate); PEG-9 to PEG-50 palmitates (CTFA names: PEG-9 palmitate to PEG-50 palmitate); PEG-9 to PEG-50 stearates (CTFA names: PEG-9 stearate to PEG-50 stearate); PEG-9 to PEG-50 palmitostearates; PEG-9 to PEG-50 behenates (CTFA names: PEG-9 behenate to PEG-50 behenate); and mixtures thereof.

Mixtures of these oxyethylenated derivatives of fatty alcohols and of fatty acids may also for example be used.

In some embodiments, the at least one anhydrous composition (A) comprises at least one ethoxylated fatty alcohol.

As non-limiting examples of monoglycerolated or polyglycerolated nonionic surfactants, monoglycerolated or polyglycerolated C8-C40 alcohols may for example be used.

In some embodiments, the monoglycerolated or polyglycerolated C8-C40 alcohols may correspond to the following formula:

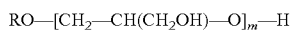

$$RO\text{—}[CH_2\text{—}CH(CH_2OH)\text{—}O]_m\text{—}H$$

wherein R represents a linear or branched $C_8$-$C_{40}$ and for example $C_8$-$C_{30}$ alkyl or alkenyl radical, and m represents a number ranging from 1 to 30 such as from 1 to 10.

As examples of compounds that may be suitable in the context of the process described herein, non-limiting mention may be made of lauryl alcohol having 4 mol of glycerol (INCI name: Polyglyceryl-4 Lauryl Ether), lauryl alcohol having 1.5 mol of glycerol, oleyl alcohol having 4 mol of glycerol (INCI name: Polyglyceryl-4 Oleyl Ether), oleyl alcohol having 2 mol of glycerol (INCI name: Polyglyceryl-2 Oleyl Ether), cetearyl alcohol having 2 mol of glycerol, cetearyl alcohol having 6 mol of glycerol, oleocetyl alcohol having 6 mol of glycerol, and octadecanol having 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, non-limiting mention may be made of the C8/C10 alcohol having 1 mol of glycerol, the C10/C12 alcohol having 1 mol of glycerol, and the $C_{12}$ alcohol having 1.5 mol of glycerol.

In some embodiments, the at least one surfactant is present in the at least one anhydrous composition (A) in an amount ranging from 0.1% to 50% by weight, such as from 0.5% to 30% by weight, relative to the weight of the at least one anhydrous composition (A).

In some embodiments, the at least one anhydrous composition (A) described herein comprises at least one alkaline agent.

The at least one alkaline agent may be chosen for example from mineral bases, organic amines, and organic amine salts, alone or as a mixture.

As regards organic amines, those whose pKb at 25° C. is less than 12, for example less than 10, such as less than 6 may for example be used. It should be noted that this is the pKb corresponding to the function of highest basicity.

Non-limiting examples of organic amines that may be mentioned are organic amines comprising one or two primary, secondary or tertiary amine functions, and at least one linear or branched C1-C8 alkyl group bearing at least one hydroxyl radical.

Organic amines chosen from alkanolamines such as mono-, di- or trialkanolamines, comprising one to three identical or different C1-C4 hydroxyalkyl radicals, may for example be used.

Among the alkanolamines that may be mentioned are for example monoethanolamine, diethanolamine, triethanolamine, monoisopropanolamine, diisopropanolamine, N-dimethylaminoethanolamine, 2-amino-2-methyl-1-propanol, tri-iso-propanolamine, 2-amino-2-methyl-1,3-propanediol, 3-amino-1,2-propanediol, 3-dimethylamino-1,2-propanediol, and tris(hydroxymethylamino)methane.

The organic amines having the following formula:

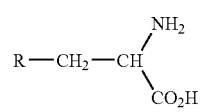

wherein W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical, may also for example be used.

Non-limiting examples of organic amines that may be mentioned include 1,3-diaminopropane, 1,3-diamino-2-propanol, spermine, and spermidine.

In some embodiments, the organic amine may be chosen from amino acids.

For example, amino acids that may be used may be of natural or synthetic origin, in L, D or racemic form, and comprise at least one acid function chosen for example from carboxylic acid, sulfonic acid, phosphonic acid, and phosphoric acid functions. The amino acids may be in their neutral or ionic form.

For example, the amino acids may be basic amino acids comprising an additional amine function optionally included in a ring or in a ureido function.

Such basic amino acids may for example be chosen from those corresponding to formula (I):

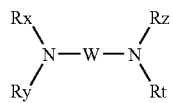

wherein R denotes a group chosen from:

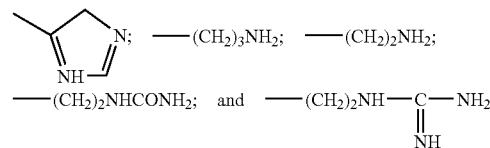

The basic amino acids corresponding to formula (I) may for example be histidine, lysine, arginine, ornithine, and citrulline.

As amino acids that may be used in the process described herein, non-limiting mention may be made for example of aspartic acid, glutamic acid, alanine, arginine, ornithine, citrulline, asparagine, carnitine, cysteine, glutamine, lysine, histidine, lysine, isoleucine, leucine, methionine, N-phenylalanine, proline, serine, taurine, threonine, tryptophan, tyrosine, and valine.

In some embodiments, the organic amine may be chosen from basic amino acids. The amino acids that may for example be used are arginine, lysine, and histidine, and mixtures thereof.

In some embodiments, the organic amine is chosen from organic amines of heterocyclic type. Besides histidine, non-limiting mention may be made for example of pyridine, piperidine, imidazole, 1,2,4-triazole, tetrazole, and benzimidazole.

In some embodiments, the organic amine may be chosen from amino acid dipeptides. As amino acid dipeptides that may be used in the process described herein, non-limiting mention may be made for example of carnosine, anserine, and baleine.

In some embodiments, the organic amine may be chosen from compounds comprising a guanidine function. As amines of this type that may be used in the process described herein, besides arginine, non-limiting mention may be made for example of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

In some embodiments, the organic amine may be chosen from alkanolamines. For example, the organic amine may be chosen from 2-amino-2-methyl-1-propanol, monoethanolamine, and mixtures thereof. For example, the organic amine may be monoethanolamine.

In some embodiments, the at least one alkaline agent may be an organic amine in salt form. As used herein, the term "organic amine salt" means organic or mineral salts of an organic amine as described above.

In some embodiments, the organic salts may for example be chosen from the salts of organic acids, such as citrates, lactates, glycolates, gluconates, acetates, propionates, fumarates, oxalates, and tartrates.

In some embodiments, the mineral salts may be chosen for example from hydrohalides (for example hydrochlorides), carbonates, hydrogen carbonates, sulfates, hydrogen phosphates, and phosphates.

As used herein, the term "mineral" means any compound bearing in its structure at least one element from columns 1 to 13 of the Periodic Table of the Elements, other than hydrogen, and not simultaneously comprising carbon and hydrogen atoms.

In some embodiments, the mineral base may contain at least one element from columns 1 and 2 of the Periodic Table of the Elements, other than hydrogen.

In some embodiments, the mineral base may have the following structure:

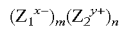

wherein $Z_2$ denotes a metal from columns 1 to 13 and for example 1 or 2 of the Periodic Table of the Elements, such as sodium or potassium;

$Z_1^{x-}$ denotes an anion chosen from the ions $CO_3^{2-}$, $OH^-$, $HCO_3^{2-}$, $SiO_3^{2-}$, $HPO_4^{2-}$, $PO_4^{3-}$, and $B_4O_7^{2-}$, and for example from the ions $CO_3^{2-}$, $OH^-$ and $SiO_3^{2-}$;

x denotes 1, 2, or 3;

y denotes 1, 2, 3, or 4;

m and n denote, independently of each other, 1, 2, 3, or 4; with (n)(y)=(m)(x).

For example, the mineral base may correspond to the formula $(Z_1^{x-})_m(Z_2^{y+})n$, wherein $Z_2$ denotes a metal from columns 1 and 2 of the Periodic Table of the Elements; $Z_1^{x-}$ denotes an anion chosen from the ions $CO_3^{2-}$, $OH^-$ and $SiO_3^{2-}$, x is 1, y denotes 1 or 2, and m and n denote, independently of each other, 1 or 2 with (n)(y)=(m)(x).

As mineral bases that may be used in the process described herein, non-limiting mention may be made of sodium bicarbonate, potassium carbonate, sodium hydroxide, potassium hydroxide, sodium metasilicates, and potassium metasilicate.

The ammonium salts that may be used in the at least one anhydrous composition (A) according to the process described herein may for example be chosen from the following acid salts: acetate, carbonate, bicarbonate, chloride, citrate, nitrate, nitrite, phosphate, sulfate. In some embodiments, the salt may be carbonate, such as ammonium carbonate.

In some embodiments, if the at least one anhydrous composition (A) comprises aqueous ammonia or one of its salts, then the amount of the at least one alkaline agent may be higher than the amount of aqueous ammonia (expressed as $NH_3$).

Generally, the at least one alkaline agent is present in the at least one anhydrous composition (A) in an amount ranging from 0.1% to 40% by weight, such as from 0.5% to 20% by weight, relative to the weight of the at least one anhydrous composition (A).

The at least one anhydrous composition (A) comprises at least one coloring or colored species chosen from at least one oxidation dye and/or at least one direct dye.

The at least one oxidation dye may for example be chosen from oxidation bases optionally combined with at least one coupler.

The at least one oxidation base may be chosen, for example, from para-phenylenediamines, bis(phenyl)alkylenediamines, para-aminophenols, ortho-aminophenols and heterocyclic bases, and the addition salts thereof.

Among the para-phenylenediamines that may be mentioned in a non-limiting manner, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)-amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylene-diamine, N-(β-hydroxypropyl)-para-phenylenediamine, 2-hydroxymethyl-para-phenylene-diamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl) pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, may for example be used.

Among the bis(phenyl)alkylenediamines that may be mentioned in a non-limiting manner, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl) tetramethylenediamine, N,N'-bis(β-hydroxyethyl)-N,N'-bis (4-aminophen-yl)tetramethylenediamine, N,N'-bis(4-methylaminophenyl)tetramethylenediamine, N,N'bis(ethyl)-N,N'-bis(4'-amino-3'-methylphenyl)ethylenediamine and 1,8-bis(2,5-diamino-phenoxy)-3,6-dioxaoctane, and the addition salts thereof.

Among the para-aminophenols that may be mentioned in a non-limiting manner, for example, are para-aminophenol, 4-amino-3-methylphenol, 4-amino-3-fluorophenol, 4-amino-3-chlorophenol, 4-amino-3-hydroxymethylphenol, 4-amino-2-methyl-phenol, 4-amino-2-hydroxymethylphenol, 4-amino-2-methoxymethylphenol, 4-amino-2-aminomethylphenol, 4-amino-2(-β-hydroxyethylaminomethyl)phenol and 4-amino-2-fluoro-phenol, and the addition salts thereof with an acid.

Among the ortho-aminophenols that may be mentioned in a non-limiting manner, for example, are 2-aminophenol, 2-amino-5-methylphenol, 2-amino-6-methylphenol and 5-acetamido-2-aminophenol, and the addition salts thereof.

Among the heterocyclic bases that may be mentioned in a non-limiting manner, for example, are pyridine derivatives, pyrimidine derivatives, and pyrazole derivatives.

Among the pyridine derivatives that may be mentioned in a non-limiting manner are the pyridine derivatives described, for example, in patents GB 1 026 978 and GB 1 153 196, for instance 2,5-diaminopyridine, 2-(4-methoxyphenyl)amino-3-amino-pyridine and 3,4-diaminopyridine, and the addition salts thereof.

Other pyridine oxidation bases that may be useful in the process described herein are the 3-aminopyrazolo[1,5-a]pyridine oxidation bases and the addition salts thereof described, for example, in patent application FR 2 801 308. Non-limiting examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]-pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxy-ethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned in a non-limiting manner are the pyrimidine derivatives described, for example, in patents DE 2 359 399; JP 88-169 571; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives that may be mentioned in a non-limiting manner are the pyrazole derivatives described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. 4,5-Diamino-1-(β-methoxyethyl)pyrazole for example may also be used.

In some embodiments, a heterocyclic base that may also be used is 2,3-diamino-6,7-dihydro-1H, 5H-pyrazolo[1,2-a]pyrazol-1-one or a salt thereof.

The at least one aqueous composition (B) described herein may optionally comprise at least one coupler, for example chosen from those conventionally used in the dyeing of keratin fibers.

Among these couplers, non-limiting mention may be made for example of meta-phenylenediamines, meta-aminophenols, meta-diphenols, naphthalene-based couplers and heterocyclic couplers, and the addition salts thereof.

Non-limiting mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methyl-indole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazo-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the at least one oxidation base and at least one coupler that may be used in the process described herein may for example be chosen from the addition salts with an acid such as the hydrochlorides, hydrobromides, sulfates, citrates, succinates, tartrates, lactates, tosylates, benzenesulfonates, phosphates, and acetates.

The at least one oxidation base may each be present in an amount ranging from 0.0001% to 10% by weight relative to the total weight of the at least one anhydrous composition (A), such as from 0.005% to 5% by weight relative to the total weight of the at least one anhydrous composition (A).

The at least one coupler, if present, may each be present in an amount ranging from 0.0001% to 10% by weight, relative to the total weight of the at least one aqueous composition (B), such as from 0.005% to 5% by weight, relative to the total weight of the at least one aqueous composition (B).

As regards the direct dyes, the at least one direct dye may for example be chosen from ionic and nonionic species, such as cationic or nonionic species.

Non-limiting examples of the at least one direct dye that may be mentioned include azo; methine; carbonyl; azine; nitro (hetero)aryl; tri(hetero)arylmethane; porphyrin; phthalocyanin direct dyes, and natural direct dyes, alone or as mixtures.

In some embodiments, the azo dyes may comprise an —N═N— function, the two nitrogen atoms of which are not simultaneously engaged in a ring. However, one of the two nitrogen atoms of the sequence —N═N— may be engaged in a ring.

The dyes of the methine family may for example be compounds comprising at least one sequence chosen from >C═C< and N═C<, the two atoms of which are not simultaneously engaged in a ring. However, one of the nitrogen or carbon atoms of the sequences may be engaged in a ring. For example, the dyes of this family may be derived from compounds of the type such as methines, azomethines, mono- and diarylmethanes, indoamines (or diphenylamines), indophenols, indoanilines, carbocyanins, azacarbocyanins and isomers thereof, diazacarbocyanins and isomers thereof, tetraazacarbocyanins and hemicyanins.

As regards the dyes of the carbonyl family, non-limiting examples that may be mentioned include dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole, and coumarin.

As regards the dyes of the cyclic azine family, non-limiting mention may be made for example of azine, xanthene, thioxanthene, fluorindine, acridine, (di)oxazine, (di)thiazine, and pyronin.

The nitro (hetero)aromatic dyes may for example be nitrobenzene or nitropyridine direct dyes.

As regards the dyes of porphyrin or phthalocyanin type, it may be possible to use cationic or noncationic compounds, optionally comprising at least one metal or metal ion, for instance alkali metals, alkaline-earth metals, zinc and silicon.

Non-limiting examples of the at least one direct dye that may be mentioned include nitrobenzene dyes; azo direct dyes; azomethine direct dyes; methine direct dyes; azacarbocyanin direct dyes, for instance tetraazacarbocyanins (tetraazapentamethines); quinone and for example anthraquinone, naphthoquinone or benzoquinone direct dyes; azine, xanthene, triarylmethane, indoamine, indigoid and phthalocyanin direct dyes, porphyrins and natural direct dyes, alone or as mixtures.

In some embodiments, these dyes may be monochromophoric dyes (i.e. comprising only one dye) or polychromophoric, such as di- or trichromophoric; the chromophores possibly being identical or different, and from the same chemical family or otherwise. It should be noted that a polychromophoric dye may comprise several radicals each derived from a molecule that absorbs in the visible region ranging from 400 to 800 nm. Furthermore, this absorbance of the dye may not require any prior oxidation thereof, or combination with any other chemical species.

In the case of polychromophoric dyes, in some embodiments, the chromophores may be connected together by means of at least one linker, which may be cationic or noncationic.

Among the benzenic direct dyes that may be used in the process described herein, mention may be made in a nonlimiting manner of the following compounds:
1,4-diamino-2-nitrobenzene,
1-amino-2-nitro-4-β-hydroxyethylaminobenzene,
1-amino-2-nitro-4-bis(β-hydroxyethyl)aminobenzene,
1,4-bis(β-hydroxyethylamino)-2-nitrobenzene,
1-β-hydroxyethylamino-2-nitro-4-bis(β-hydroxyethylamino)benzene,
1-β-hydroxyethylamino-2-nitro-4-aminobenzene,
1-β-hydroxyethylamino-2-nitro-4-(ethyl)(β-hydroxyethyl)aminobenzene,
1-amino-3-methyl-4-β-hydroxyethylamino-6-nitrobenzene,
1-amino-2-nitro-4-β-hydroxyethylamino-5-chlorobenzene,
1,2-diamino-4-nitrobenzene,
1-amino-2-β-hydroxyethylamino-5-nitrobenzene,
1,2-bis(β-hydroxyethylamino)-4-nitrobenzene,
1-amino-2-tris(hydroxymethyl)methylamino-5-nitrobenzene,
1-hydroxy-2-amino-5-nitrobenzene,
1-hydroxy-2-amino-4-nitrobenzene,
1-hydroxy-3-nitro-4-aminobenzene,
1-hydroxy-2-amino-4,6-dinitrobenzene,
1-β-hydroxyethyloxy-2-β-hydroxyethylamino-5-nitrobenzene,
1-methoxy-2-β-hydroxyethylamino-5-nitrobenzene,
1-β-hydroxyethyloxy-3-methylamino-4-nitrobenzene,
1-β,γ-dihydroxypropyloxy-3-methylamino-4-nitrobenzene,
1-β-hydroxyethylamino-4-β,γ-dihydroxypropyloxy-2-nitrobenzene,
1-β,γ-dihydroxypropylamino-4-trifluoromethyl-2-nitrobenzene,
1-β-hydroxyethylamino-4-trifluoromethyl-2-nitrobenzene,
1-β-hydroxyethylamino-3-methyl-2-nitrobenzene,
1-β-aminoethylamino-5-methoxy-2-nitrobenzene,
1-hydroxy-2-chloro-6-ethylamino-4-nitrobenzene,
1-hydroxy-2-chloro-6-amino-4-nitrobenzene,
1-hydroxy-6-bis(β-hydroxyethyl)amino-3-nitrobenzene,
1-β-hydroxyethylamino-2-nitrobenzene, and
1-hydroxy-4-β-hydroxyethylamino-3-nitrobenzene.

Among the azo, azomethine, methane, and tetraazapentamethine direct dyes that may be used in the process described herein, non-limiting mention may be made of the cationic dyes described in patent applications WO 95/15144, WO 95/01772 and EP 714 954; FR 2 189 006, FR 2 285 851, FR 2 140 205, EP 1 378 544 and EP 1 674 073.

Non-limiting mention may also be made of the following compounds:

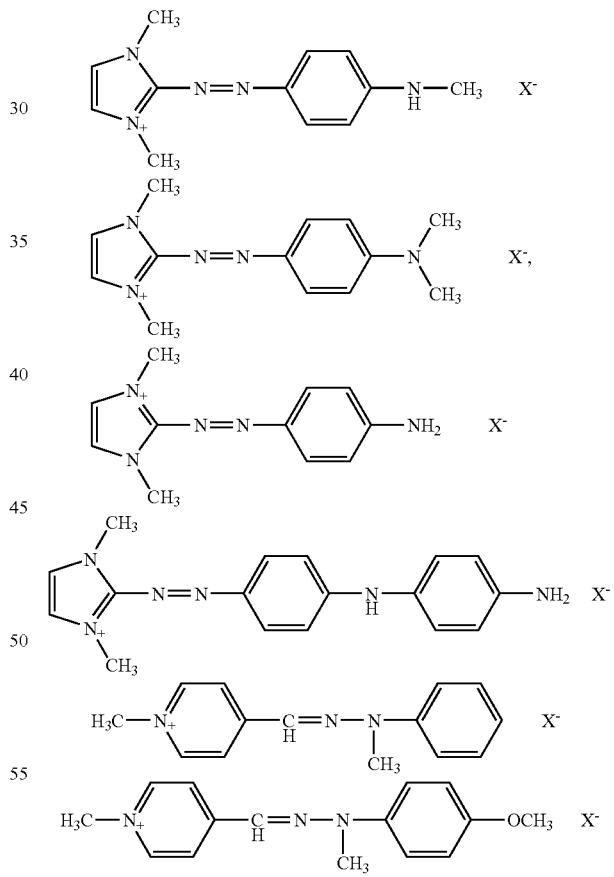

Among the azo direct dyes that may also be mentioned in a non-limiting manner are the following dyes, described in the Color Index International, 3rd edition:
Disperse Red 17
Basic Red 22
Basic Red 76
Basic Yellow 57

Basic Brown 16
Basic Brown 17
Disperse Black 9.

Non-limiting mention may also be made of 1-(4'-aminodiphenylazo)-2-methyl-4-bis(β-hydroxyethyl)aminobenzene.

Among the quinone direct dyes that may be mentioned in a non-limiting manner are the following dyes:
Disperse Red 15
Solvent Violet 13
Disperse Violet 1
Disperse Violet 4
Disperse Blue 1
Disperse Violet 8
Disperse Blue 3
Disperse Red 11
Disperse Blue 7
Basic Blue 22
Disperse Violet 15
Basic Blue 99 and also the following compounds:
    1-N-methylmorpholiniumpropylamino-4-hydroxyanthraquinone
    1-aminopropylamino-4-methylaminoanthraquinone
    1-aminopropylaminoanthraquinone
    5-β-hydroxyethyl-1,4-diaminoanthraquinone
    2-aminoethylaminoanthraquinone
    1,4-bis(β,γ-dihydroxypropylamino)anthraquinone.

Among the azine dyes that may be mentioned in a non-limiting manner are the following compounds:
Basic Blue 17
Basic Red 2.

Among the triarylmethane dyes that may be used in the process described herein, non-limiting mention may be made of the following compounds:
Basic Green 1
Basic Violet 3
Basic Violet 14
Basic Blue 7
Basic Blue 26.

Among the indoamine dyes that may be used in the process described herein, non-limiting mention may be made of the following compounds:
    2-β-hydroxyethylamino-5-[bis(β-4'-hydroxyethyl)amino]anilino-1,4-benzoquinone
    2-β-hydroxyethylamino-5-(2'-methoxy-4'-amino)anilino-1,4-benzoquinone
    3-N-(2'-chloro-4'-hydroxy)phenylacetylamino-6-methoxy-1,4-benzoquinone imine
    3-N-(3'-chloro-4'-methylamino)phenylureido-6-methyl-1,4-benzoquinone imine
    3-[4'-N-(ethyl,carbamylmethyl)amino]phenylureido-6-methyl-1,4-benzoquinone imine.

Among the dyes of tetraazapentamethine type that may be used in the process described herein, non-limiting mention may be made of the following compounds given in the table below, $X^-$ being defined as previously:

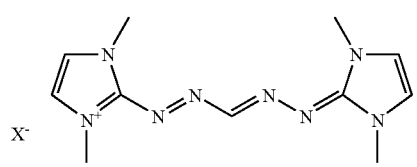

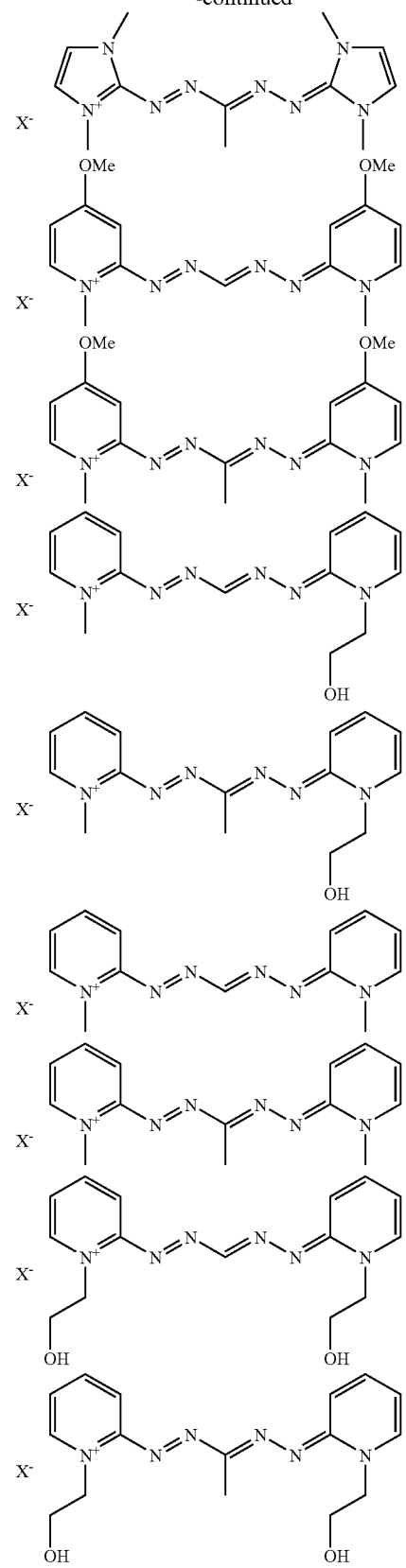

$X^-$ represents an anion for example chosen from chloride, iodide, methyl sulfate, ethyl sulfate, acetate, and perchlorate.

Among the polychromophoric dyes, non-limiting reference may be made for example to patent applications EP 1 637 566, EP 1 619 221, EP 1 634 926, EP 1 619 220, EP 1 672 033, EP 1 671 954, EP 1 671 955, EP 1 679 312, EP 1 671 951, EP 167 952, EP 167 971, WO 06/063 866, WO 06/063 867, WO 06/063 868, WO 06/063 869, EP 1 408 919, EP 1 377 264, EP 1 377 262, EP 1 377 261, EP 1 377 263, EP 1 399 425, EP 1 399 117, EP 1 416 909, EP 1 399 116 and EP 1 671 560.

In some embodiments, it may also be possible to use the cationic direct dyes mentioned for example in patent applications: EP 1 006 153, which describes dyes comprising two chromophores of anthraquinone type connected via a linker of cationic type; EP 1 433 472, EP 1 433 474, EP 1 433 471 and EP 1 433 473, which describe identical or different dichromophoric dyes, connected via a cationic or noncationic linker, and also EP 6 291 333, which for example describes dyes comprising three chromophores, one of them being an anthraquinone chromophore, to which are attached two chromophores of azo or diazacarbocyanin type or an isomer thereof.

Among the natural direct dyes that may be used in the process described herein, non-limiting mention may be made of lawsone, juglone, alizarin, purpurin, carminic acid, kermesic acid, purpurogallin, protocatechaldehyde, indigo, isatin, curcumin, spinulosin, apigenidin and orceins. It may also be possible to use extracts or decoctions comprising these natural dyes and for example henna-based poultices or extracts.

When present, the at least one direct dye may be present in an amount ranging from 0.0001% to 10% by weight, such as from 0.005% to 5% by weight, relative to the total weight of the at least one anhydrous composition (A).

In some embodiments, the at least one anhydrous composition (A) may comprise one and/or the other types of dyes. It may optionally correspond to two dye compositions, one comprising the at least one oxidation dye, the other the at least one direct dye, which are mixed at the moment of use.

In some embodiments, the at least one anhydrous composition (A) may comprise at least one water-soluble organic solvent. Non-limiting examples of water-soluble organic solvents that may be mentioned include linear or branched C2-C4 alkanols, such as ethanol and isopropanol; polyols and polyol ethers, for instance 2-butoxyethanol, glycerol, propylene glycol, dipropylene glycol, polyethylene glycols, propylene glycol monomethyl ether, diethylene glycol monomethyl ether and monoethyl ether, and also aromatic alcohols, for instance benzyl alcohol or phenoxyethanol, and mixtures thereof. The expression "water-soluble solvent" is understood to mean a compound that is liquid at 25° C. and at atmospheric pressure (760 mm of mercury) and at least 5% soluble in water under these conditions.

In some embodiments, the at least one anhydrous composition (A) may also contain various adjuvants conventionally used in hair lightening compositions, such as anionic, cationic, nonionic, amphoteric or zwitterionic polymers or mixtures thereof; mineral thickeners, and for example fillers such as clays, talc; organic thickeners with, for example, anionic, cationic, nonionic and amphoteric polymeric associative thickeners; antioxidants; penetrants; sequestrants; fragrances; dispersants; film-forming agents; preserving agents; and opacifiers.

In some embodiments, the at least one anhydrous composition (A) comprises at least one stabilizing polymer. In some embodiments, the at least one stabilizing polymer may be chosen from cellulose polymers and for example nonionic, cationic or anionic, for example cationic, cellulose ethers. The at least one stabilizing polymer may or may not be associative. As a non-associative cellulose ether, non-limiting mention may be made of hydroxyethyl or hydroxypropyl cellulose. As an associative cellulose ether, non-limiting mention may be made of cetyl hydroxyethyl celluloses.

In some embodiments, the at least one anhydrous composition (A) may be a direct oil-in-at-least-one-water-soluble-solvent emulsion.

The process described herein is performed with at least one aqueous composition (B) comprising at least one oxidizing agent.

In some embodiments, the at least one oxidizing agent may be chosen from hydrogen peroxide, urea peroxide, alkali metal bromates or ferricyanides, and peroxygenated salts, for instance alkali metal or alkaline-earth metal persulfates, perborates peracids and precursors thereof, and percarbonates.

The at least one oxidizing agent may for example be constituted by hydrogen peroxide, for instance as an aqueous solution (aqueous hydrogen peroxide solution), the titer of which may range from 1 to 40 volumes (0.3% to 12% of $H_2O_2$), such as from 5 to 40 volumes (1.5% to 12% of $H_2O_2$).

As a function of the desired degree of lightening, the at least one aqueous composition (B) may also, in some embodiments, comprise, besides the hydrogen peroxide, at least one additional oxidizing agent chosen for example from peroxygenated salts.

The at least one aqueous composition (B) is generally an aqueous composition. The term "aqueous composition" means, as used herein, a composition comprising water present in an amount of greater than 20% by weight, for example more than 30% by weight, such as more than 40% by weight, relative to the total weight of the at least one aqueous composition (B).

The at least one aqueous composition (B) may also comprise at least one water-soluble organic solvent as described above. In some embodiments, it may also comprise at least one acidifying agent.

Non-limiting examples of acidifying agents that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

In some embodiments, the pH of the at least one aqueous composition (B) may be less than 7.

In some embodiments, the at least one aqueous composition (B) may be in various forms, for instance a solution, an emulsion, or a gel.

Also provided is a process for dyeing keratin materials, comprising applying to the keratin materials:
a) at least one anhydrous composition (A) comprising at least one fatty substance, at least one surfactant, at least one alkaline agent, and at least one colored or coloring species; and
b) at least one aqueous composition (B) comprising at least one oxidizing agent
wherein:
   the at least one fatty substance is present in the at least one anhydrous composition (A) in an amount of greater than 20% by weight, relative to the total weight of the at least one anhydrous composition (A); and
   the at least one colored or coloring species comprises at least one oxidation dye and/or at least one direct dye;
   provided that when the at least one anhydrous composition (A) comprises, as the at least one colored or coloring species, only at least one direct dye, the at least one fatty substance is present in an amount ranging from 40 to 80% by weight, relative to the total weight of the at least one anhydrous composition (A);

further wherein the at least one anhydrous composition (A) and the at least one aqueous composition (B) are applied to the keratin materials, successively and without intermediate rinsing, in any order.

Also provided is a process for dyeing keratin materials, comprising applying, to wet or dry keratin materials, a resultant composition obtained by extemporaneously mixing, at the time of use, the at least one anhydrous composition (A) and the at least one aqueous composition (B). The process for dyeing keratin materials thus comprises applying to the keratin materials:

a) at least one anhydrous composition (A) comprising at least one fatty substance, at least one surfactant, at least one alkaline agent, and at least one colored or coloring species; and b) at least one aqueous composition (B) comprising at least one oxidizing agent wherein:

the at least one fatty substance is present in the at least one anhydrous composition (A) in an amount of greater than 20% by weight, relative to the total weight of the at least one anhydrous composition (A); and the at least one colored or coloring species comprises at least one oxidation dye and/or at least one direct dye;

provided that when the at least one anhydrous composition (A) comprises, as the at least one colored or coloring species, only at least one direct dye, the at least one fatty substance is present in an amount ranging from 40 to 80% by weight, relative to the total weight of the at least one anhydrous composition (A);

wherein applying to the keratin materials further comprises:

mixing, at the time of use, the at least one anhydrous composition (A) and the at least one aqueous composition (B); and applying the resultant composition to the keratin materials. According to this embodiment, the at least one anhydrous composition (A) and the at least one aqueous composition (B) may be present at a weight ratio ranging from 0.1 to 10, for example from 0.2 to 2, such as from 0.3 to 1.

In some embodiments, the resultant composition obtained after mixing the at least one anhydrous composition (A) and the at least one aqueous composition (B) described herein, is such that, after the mixture, the at least one fatty substance is present in an amount of greater than 20% by weight, for example greater than 25%, such as greater than 30% by weight, relative to the weight of the resultant composition.

In addition, the mixture applied to the keratin materials (resulting either from the extemporaneous mixing of (A) and (B) or from the partial or total successive application thereof) may be left in place for a period of time, for example ranging from 1 minute to 1 hour, such as from 5 minutes to 30 minutes.

The temperature during the process may for example range from room temperature (for instance from 15 to 25° C.) to 80° C. and for example from room temperature to 60° C.

After the treatment, the keratin materials may optionally be rinsed with water, optionally washed and then rinsed with water, before being dried or left to dry.

In some embodiments, the keratin materials may be human hair.

Also provided is a multi-compartment device comprising:
a first compartment comprising at least one anhydrous composition (A) comprising at least one fatty substance, at least one surfactant, at least one alkaline agent, and at least one colored or coloring species; and a second compartment comprising at least one aqueous composition (B) comprising at least one oxidizing agent;

wherein:

the at least one fatty substance is present in the at least one anhydrous composition (A) in an amount of greater than 20% by weight, relative to the total weight of the at least one anhydrous composition (A); and the at least one colored or coloring species comprises at least one oxidation dye and/or at least one direct dye;

on the condition that when the at least one anhydrous composition (A) comprises, as the at least one colored or coloring species, only at least one direct dye, the at least one fatty substance is present in an amount ranging from 40 to 80% by weight, relative to the total weight of the at least one anhydrous composition (A).

The following examples illustrate the disclosure but are not in any way limiting.

EXAMPLES

Example 1

The following composition was prepared:

| Composition A1 | g % |
|---|---|
| Pure monoethanolamine | 4 |
| Glycerol | 45 |
| Polyglycerolated lauryl cetylstearyl glycol (6 mol) sold under the name Chimexane NS | 1% |
| Liquid petroleum jelly | 50% |
| Resorcinol | 0.5% |
| Para-phenylenediamine | 0.5% |
| Sodium metabisulfite | 0.2% |

At the time of use, composition A1 (direct oil-in-water soluble solvent emulsion) was mixed weight for weight with at least one oxidizing aqueous composition (B) comprising 20 volumes of $H_2O_2$ and at pH 2.2.

The mixture was then applied to a lock of natural chestnut-brown hair (tone height=4). The bath ratio "mixture/lock" was 10/1 (g/g). The leave-on time was 30 minutes at 27° C. After the leave-on time, the locks were rinsed and then washed with Elsève multivitamin shampoo, rinsed and dried.

Example 2

The following composition was prepared:

| Composition A2 | g % |
|---|---|
| Pure monoethanolamine | 4 |
| Liquid petroleum jelly | 50 |
| PEG-8 | 32 |
| Hydroxypropyl cellulose Klucel EF Pharm sold by Aqualon | 4 |
| Oleth-10 | 10 |
| Para-phenylenediamine | 0.5% |
| Resorcinol | 0.5% |

At the time of use, composition A2 was mixed weight for weight with an oxidizing aqueous composition (B2) comprising 20 volumes of $H_2O_2$ and at pH 2.2.

The mixture was then applied to a lock of natural chestnut-brown hair (tone height=4). The bath ratio "mixture/lock" was, respectively, 10/1 (g/g). The leave-on time was 30 minutes at 27° C. After the leave-on time, the locks were rinsed and then washed with Elsève multivitamin shampoo, rinsed and dried.

Results

The inventive emulsions A1 and A2 did not give off a disagreeable odor, even after mixing with the oxidizing composition. Furthermore, the levels of lightening obtained with the inventive emulsions were acceptable, of the same level as the conventional ammonia-containing lightening compositions. The dark blonde shades obtained in both cases were not very selective, which is representative of a homogeneity of coloration along the keratin fiber.

What is claimed is:

1. A process for dyeing keratin materials, comprising applying to the keratin materials:
    a) at least one anhydrous composition (A) comprising at least one fatty substance, at least one surfactant, at least one alkaline agent, and at least one colored or coloring species; and
    b) at least one aqueous composition (B) comprising at least one oxidizing agent;
    wherein:
        the at least one fatty substance is present in the at least one anhydrous composition (A) in an amount of greater than 20% by weight, relative to the total weight of the at least one anhydrous composition (A); and
        the at least one colored or coloring species comprises at least one oxidation dye and/or at least one direct dye;
        provided that when the at least one anhydrous composition (A) comprises, as the at least one colored or coloring species, only at least one direct dye, the at least one fatty substance is present in an amount ranging from 40 to 80% by weight, relative to the total weight of the at least one anhydrous composition (A).

2. The process according to claim 1, wherein the at least one fatty substance is present in the at least one anhydrous composition (A) in an amount ranging from 40% to 80% by weight, relative to the total weight of the at least one anhydrous composition.

3. The process according to claim 1, wherein the at least one fatty substance is chosen from liquid and pasty compounds.

4. The process according to claim 1, wherein the at least one fatty substance is chosen from compounds that are liquid at room temperature and at atmospheric pressure.

5. The process according to claim 1, wherein the at least one fatty substance is chosen from $C_6$-$C_{16}$ alkanes, fatty alcohols, fatty acids, fatty acid esters, fatty alcohol esters, mineral oils of more than 16 carbon atoms, non-silicone plant, animal or synthetic oils, silicones, and non-silicone waxes.

6. The process according to claim 1, wherein the at least one fatty substance is chosen from liquid petroleum jelly, polydecenes, esters of liquid fatty alcohols or fatty acids and mixtures thereof.

7. The process according to claim 1, wherein the at least one surfactant is at least one nonionic surfactant chosen from monooxyalkylenated, polyoxyalkylenated, monoglycerolated, and polyglycerolated nonionic surfactants.

8. The process according to claim 1, wherein the at least one alkaline agent is chosen from organic amines, mineral bases, organic amine salts, and ammonium salts.

9. The process according to claim 8, wherein the at least one alkaline agent is chosen from alkanolamines.

10. The process according to claim 1, wherein the at least one alkaline agent is chosen from 2-amino-2-methyl-1-propanol, monoethanolamine, and mixtures thereof, and basic amino acids chosen from arginine, histidine, lysine, and mixtures thereof.

11. The process according to claim 1, wherein the at least one anhydrous composition (A) further comprises at least one associative or non-associative cellulose ether.

12. The process according to claim 1, wherein the at least one anhydrous composition (A) further comprises at least one water-soluble solvent.

13. The process according to claim 12, wherein the at least one anhydrous composition (A) is an anhydrous direct oil-in-at-least-one-water-soluble solvent emulsion.

14. The process according to claim 1, wherein the at least one oxidation dye is chosen from para-phenylenediamines, bis(phenyl)alkylenediamines, para-aminophenols, ortho-aminophenols, heterocyclic bases, and the addition salts thereof, meta-phenylenediamines, meta-aminophenols, meta-diphenols, naphthalene-based couplers, heterocyclic couplers and the addition salts thereof.

15. The process according to claim 1, wherein the at least one direct dye is chosen from azo; methine; carbonyl; azine; nitro(hetero)aryl; tri(hetero)arylmethane; porphyrin; phthalocyanin direct dyes, and natural direct dyes, alone or as mixtures.

16. The process according to claim 1, wherein the at least one oxidizing agent is chosen from hydrogen peroxide, urea peroxide, alkali metal bromates or ferricyanides, peroxygenated salts, and percarbonates.

17. The process according to claim 16, wherein the at least one oxidizing agent is chosen from alkali metal or alkaline-earth metal persulfates, perborates, peracids, and the precursors thereof.

18. The process according to claim 16, wherein the at least one oxidizing agent is hydrogen peroxide.

19. The process according to claim 1, wherein the at least one aqueous composition (B) comprises water, present in an amount of greater than 20% by weight, relative to the total weight of the at least one aqueous composition (B).

20. The process according to claim 19, wherein the at least one aqueous composition (B) comprises water, present in an amount of greater than 30%, relative to the total weight of the at least one aqueous composition (B).

21. The process according to claim 20, wherein the at least one aqueous composition (B) comprises water, present in an amount of greater than 40%, relative to the total weight of the at least one aqueous composition (B).

22. The process according to claim 1, wherein applying to the keratin materials further comprises:
    mixing, at the time of use, the at least one anhydrous composition (A) and the at least one aqueous composition (B); and
    applying the resultant composition to the keratin materials.

23. The process according to claim 1, wherein the at least one anhydrous composition (A) and the at least one aqueous composition (B) are applied to the keratin materials, successively and without intermediate rinsing, in any order.

24. The process according to claim 1, wherein the keratin materials are human hair.

25. A multi-compartment device comprising:
    a first compartment comprising at least one anhydrous composition (A) comprising at least one fatty substance, at least one surfactant, at least one alkaline agent, and at least one colored or coloring species; and a second compartment comprising at least one aqueous composition (B) comprising at least one oxidizing agent;

wherein:

the at least one fatty substance is present in the at least one anhydrous composition (A) in an amount of greater than 20% by weight, relative to the total weight of the at least one anhydrous composition (A); and the at least one colored or coloring species comprises at least one oxidation dye and/or at least one direct dye;

provided that when the at least one anhydrous composition (A) comprises, as the at least one colored or coloring species, only at least one direct dye, the at least one fatty substance is present in an amount ranging from 40 to 80% by weight, relative to the total weight of the at least one anhydrous composition (A).

* * * * *